United States Patent [19]
Baldwin, III

[11] 4,044,773
[45] Aug. 30, 1977

[54] COLD THERAPEUTIC PACKAGE

[76] Inventor: Henry Clay Baldwin, III, 429 S. Bolmar St., West Chester, Pa. 19380

[21] Appl. No.: 608,270

[22] Filed: Aug. 27, 1975

[51] Int. Cl.² .............................................. A61F 7/04
[52] U.S. Cl. ..................................... 128/402; 128/403
[58] Field of Search ............... 128/402, 403, 399, 258, 128/379, 382

[56] References Cited

U.S. PATENT DOCUMENTS

| 3,075,529 | 1/1963 | Young | 128/403 |
| 3,506,013 | 4/1970 | Zdenek | 128/402 |
| 3,762,419 | 10/1973 | Walters | 128/403 |
| 3,822,705 | 7/1974 | Pilotte | 128/379 |

Primary Examiner—Lawrence W. Trapp
Attorney, Agent, or Firm—Weiser, Stapler & Spivak

[57] ABSTRACT

Two sheets of polyurethane film are sealed together to form a hollow interior within which water can be frozen into a layer thin enough to be cracked into small ice fragments. The package containing cracked ice is applied to the area to be treated.

5 Claims, 5 Drawing Figures

COLD THERAPEUTIC PACKAGE

This invention relates to devices for treating ailments by the local application of a cold medium.

While not limited thereto, the invention is particularly useful in the treatment of certain ailments affecting race horses, which require the application of cold compresses to their limbs. It should be noted that the present invention is not concerned with the medical aspects of such treatment, i.e. with the indications requiring it or with its therapeutic efficacy, but only with the mechanical device for administering it.

Many devices have previously been proposed for this type of treatment. These typically include some type of bag containing a fluid medium. This medium is cooled, either before or after it is placed in the bag, and the bag with its contents is then applied to the area to be treated. In the case of a horse's limb, the bag may be of generally flat, rectangular shape, and applied by being wrapped around the limb and retained in place with straps, or other fastening means.

Such prior art devices, while obviously useful to some degree for their intended purposes, have nevertheless fallen short of the ideal in various respects.

In particular, the effectiveness with which the desired cold was transferred to all parts of the area to be treated left something to be desired.

The materials of which the prior art devices were made were sometimes quite unsatisfactory from the heat transfer standpoint, thereby counteracting the very purpose of the device.

The degree to which the device conformed to differently shaped portions of the affected area was often less than complete, lessening the intimacy of cold application, and so forth.

Accordingly, it is a primary object of the present invention to provide a cold therapeutic device which overcomes one or more of the imperfections of prior art devices.

It is another object to provide a cold therapeutic device which is capable of conforming exceptionally well to the contours of the area to be affected.

It is still another object to provide a cold therapeutic device which is made of material having exceptionally desirable heat transfer characteristics.

It is a still further object to provide such a device having other desirable properties, as to strength, durability and ease of manufacture.

These and other objects which will appear are achieved in accordance with the present invention by providing a device in the form of two generally planar sheets of polyurethane film. The two sheets are sealed together around their edges to define a hollow interior. This interior is partially filled with a fluid, such as water, which is a liquid at room temperature, but turns reversibly into a solid at a suitable lower temperature.

The outer dimensions of the two sheets are so chosen that the device can be wrapped around the area to be subject to cold therapy, e.g. the limb of a horse, and fasteners are preferably attached to the sheets to hold the wrapped device closed upon itself.

The dimensions of the hollow interior are so chosen that the solid into which the contents turn when cooled is thin enough to be brittle and readily cracked and fragmented into small pieces.

For further details reference is made to the discussion which follows, in the light of the accompanying drawings wherein:

FIG. 1 shows a device embodying this invention as used in a typical application on the limb of a horse;

FIGS. 2 and 3 each show a plan view, partly cut away to show the interior, of an embodiment of the invention;

The same reference numerals are used in the different figures to designate similar elements.

Figure 2:
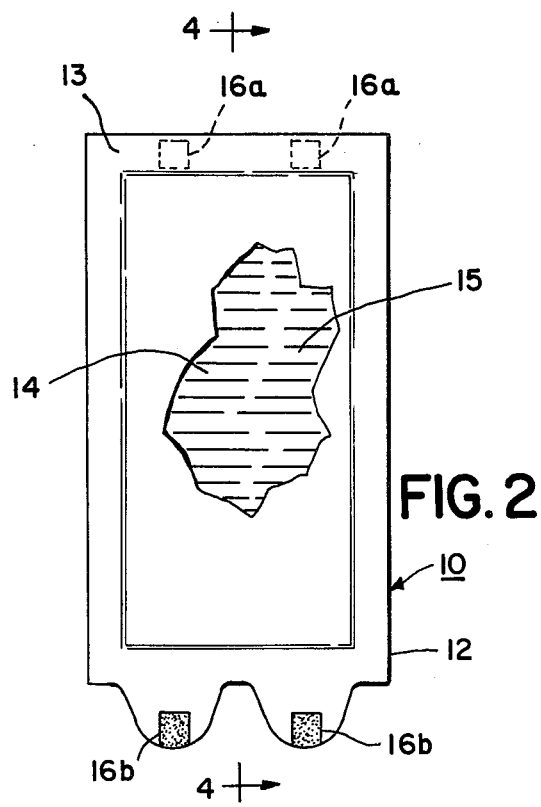
Figures 4, 5:
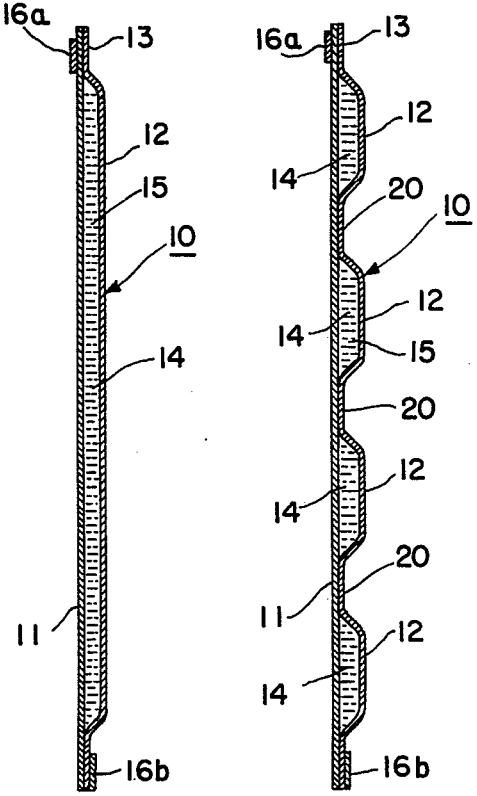
FIG. 4 shows in cross-section the embodiment of FIGS. 2 and 3.
FIG. 5 shows a cross-sectional view of another embodiment of the invention.

Referring first to FIGS. 2 and 4, these show in plan view and cross-sectional view, respectively, a cold therapeutic device embodying the present invention. The device is formed of two generally parallel sheets 11 and 12 (see particularly FIG. 4) of a material whose characteristics are described in detail below. Only sheet 12 of this material is visible in FIG. 2. The two sheets are sealed together around the periphery of the device in the area designated by reference numeral 13.

The two sheets 11 and 12 are so dimensioned that they form between them hollow interior 14 (see FIG. 4), a portion of which is also visible in the cut-away section of the plan view of FIG. 2. A suitable liquid, such as water, is placed in this hollow interior 14 before the sealing of the edge portion 13 is completed. The relationship between the hollow interior 14 and the quantity of water 15 placed therein is such that the water 15 does not completely fill the hollow interior 14 at room temperature. Rather, at least enough of the hollow interior 14 is left unfilled to allow for expansion of the water when it is frozen into ice without rupture of the sheets 11 and 12. At opposite ends of the device 10, there are applied tabs 16a and 16b which are suitable for providing temporary adhesion to each other when placed in contact.

Tabs 16a are attached to one side of the device, namely to the exposed side of sheet 11, while tabs 16b are attached to the opposite side of the device, namely to the exposed side of sheet 12. These tabs 16a and 16b are preferably of a material such as the temporarily adhering material known as "Velcro", which is formed of tightly crinkled, stiff fibers which tend to interlace and resist separation when two surfaces of the same material are pressed together.

Figure 1:
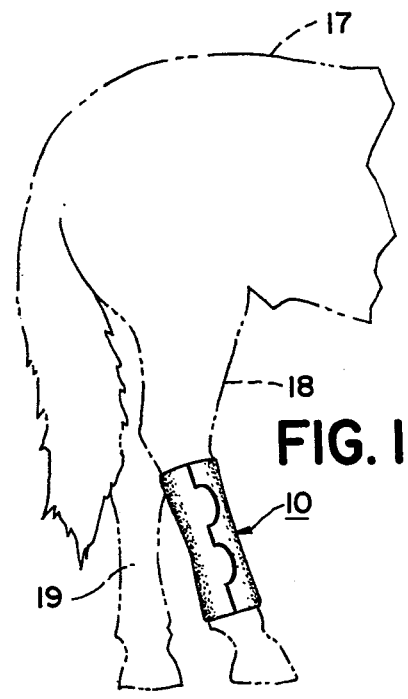

The manner in which the device of FIGS. 2 and 4 is applied to the area to be subjected to cold treatment is typified in FIG. 1, to which reference may now be had. This figure shows diagrammatically the hind portion of a horse 17 including its rear legs 18, 19. The device 10 of FIGS. 2 and 4 is shown wrapped around the lower portion of leg 18. The protruding tab portions 16b have been used to engage the corresponding tab portions 16a (none of which are visible in FIG. 1), thereby closing the device of FIG. 1 upon itself in the generally cylindrical shape shown in FIG. 1 and securing it in place on the limb 18.

Figure 3:
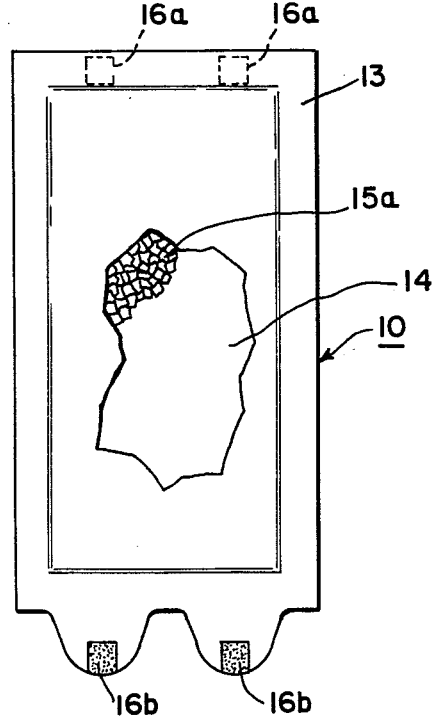

Before being applied to the area to be subjected to cold treatment as shown in FIG. 1, the device of FIGS. 2 and 4 has been subjected itself to a pre-treatment, which transforms it into the condition illustrated in FIG. 3, to which reference may now be had.

The interior 14 of the device 10, a portion of which is visible through the cut-away portion of top sheet 12, is seen to contain many small pieces of ice 15a, rather than the water 15 present in the illustration of FIG. 2. This transformation has been accomplished by placing the device of FIG. 2, preferably flattened out to obtain generally uniform distribution of the water within the hollow interior 14 defined between sheets 11 and 12, in an environment sufficiently cold to turn this water into ice.

Thereafter, the device, with the water now turned into ice in its interior 14, has been flexed and deformed sufficiently to subdivide into the small particles of ice 15a, the much larger sheets of ice which have typically formed in the interior 14 when the entire device 10 was subjected to a freezing atmosphere.

Such subdividing into small ice particles is accomplished either by rolling the device up first along one of its long axes and then at right angles thereto, or by striking against a hard edge, such as the edge of a table or workbench repeatedly along different lines traversing the surface of sheets 11 and 12.

It is with the ice content finely subdivided as shown in FIG. 3 that the device 10 is then applied to the area to be subjected to cold treatment as, for example, illustrated in FIG. 1.

An alternative embodiment of the device embodying the present invention is illustrated in FIG. 5, to which reference may now be had.

This embodiment differs from that of FIGS. 2 to 4 in that sheet 12 is sealed to sheet 11 not only around the edge portions 13 but also at intermediate portions 20, thereby essentially subdividing the hollow interior 14 into a plurality of separate portions separated by sealed areas 20. In all other respects, the embodiment of FIG. 5 may be similar to that of FIGS. 2 to 4, including its treatment prior to application to the area to be cold-treated, and also its mode of application and utilization.

It will be understood that the overall dimensions of the device 10 will be so selected as to make the device conveniently applicable to the area to be subjected to cold treatment.

The material of which the sheets 11 and 12 are made is preferably a polyurethane ester film, such as is available from J. P. Stevens and Co., Inc. of Easthampton, Massachusetts 01027, under stock numbers MP-2080, MP-1885 and MP-1880. Preferably the film available under the stock number MP-1885 is utilized. This film, which is available in various thicknesses, is preferably used with a thickness in the range between twenty and thirty thousandths of an inch. The relative dimensions of sheets 11 and 12 made of such film are preferably such that a spacing of approximately ⅛ to ¼ inch exists between the sheets defining the interior 14. This permits rapid freezing of the water 15 in the interior into ice and convenient subdivision of that ice into small ice particles 15a.

The fact that the ice is subdivided into such small particles before application of the device to the area to be treated has two advantages. First, the presence of the ice in small particles increases the surface area of the ice and with it the ability of that ice to absorb heat from the area to be treated. Secondly, and possibly even more importantly, the subdivision of the ice into small particles enables the device to locally conform to variations in the contour of the area to be treated. At the same time, the fact that the contents of the ice are a solid and not a liquid prevents these contents from accumulating at that end of the device to which gravity would otherwise direct such an accumulation. Therefore, more uniform distribution of the cold is maintained over the area which has been treated.

As for the polyurethane film material, this not only has exceptionally desirable properties from all of the physical standpoints, such as tear strength, elasticity, and so forth, but it also exhibits exceptionally desirable characteristics with respect to heat transmissivity. Therefore it does not provide an unwanted barrier to the functioning of the device in cold treatment.

It will be understood that many variations of the device will occur to those skilled in the art without departing from the inventive concept.

Also it will be understood that the usefulness of the device is not limited to the treatment of any particular type of area, but can be used for human treatment and for any other purpose for which cold treatment is indicated.

To that end, if necessary, the overall shape of the device and its fastening techniques may also be varied to suit.

I claim:

1. The method of using a cold therapeutic package for local treatment, said package having a longitudinal axis, comprising the steps of
    forming a generally flat layer of ice between sheets of polyurethane film materials;
    fragmenting the layer of ice into a plurality of small, finely subdivided, randomly shaped and sized particles;
    applying the package about an area to be treated; and
    conforming the film materials and the fragmented particles to the contours of the area to be treated.

2. The method of claim 1 wherein the fragmenting is accomplished by rolling the film materials along the longitudinal axis.

3. The method of claim 2 wherein further fragmenting is accomplished by rolling the film materials along an axis that is angularly offset from the said longitudinal axis.

4. The method of claim 1 wherein the fragmenting is accomplished by striking the film material against a hard edge.

5. The method of claim 4 wherein the striking is repeated until the layer is broken sufficiently to form the small, randomly shaped particles.

* * * * *